US011114603B2

(12) United States Patent
Chaggares et al.

(10) Patent No.: US 11,114,603 B2
(45) Date of Patent: Sep. 7, 2021

(54) MEDICAL INSTRUMENT INCLUDING HIGH FREQUENCY ULTRASOUND TRANSDUCER ARRAY

(71) Applicant: FUJIFILM SonoSite, Inc., Bothell, WA (US)

(72) Inventors: Nicholas Christopher Chaggares, Whitby (CA); Desmond Hirson, Thornhill (CA); Oleg Ivanytskyy, Toronto (CA); Guofeng Pang, Ajax (CA); Robert J. Kolaja, Toronto (CA)

(73) Assignee: FUJIFILM SONOSITE, INC., Bothell, VA (US)

( * ) Notice: Subject to any disclaimer, the term of this patent is extended or adjusted under 35 U.S.C. 154(b) by 1165 days.

(21) Appl. No.: 15/359,600

(22) Filed: Nov. 22, 2016

(65) Prior Publication Data

US 2017/0143297 A1 May 25, 2017

Related U.S. Application Data

(60) Provisional application No. 62/260,219, filed on Nov. 25, 2015.

(51) Int. Cl.
*A61B 8/12* (2006.01)
*A61B 8/00* (2006.01)
(Continued)

(52) U.S. Cl.
CPC ............... *H01L 41/00* (2013.01); *A61B 8/12* (2013.01); *B06B 1/0622* (2013.01);
(Continued)

(58) Field of Classification Search
CPC ............................... B06B 1/0622; A61B 8/12
See application file for complete search history.

(56) References Cited

U.S. PATENT DOCUMENTS 5,456,259 A * 10/1995 Barlow ................ A61B 8/12
600/459
5,575,288 A 11/1996 Sliwa, Jr. et al.
(Continued)

FOREIGN PATENT DOCUMENTS

| CN | 1643624 A | 7/2005 |
| CN | 101396289 A | 4/2009 |

(Continued)

OTHER PUBLICATIONS

International Searching Authority, International Search Report and Written Opinion, PCT Application PCT/US2016/063433, dated Feb. 14, 2017, 14 pages.

(Continued)

*Primary Examiner* — Michael J Tsai
*Assistant Examiner* — Johnathan Maynard
(74) *Attorney, Agent, or Firm* — Baker Botts L.L.P.

(57) ABSTRACT

Disclosed is a medical device that includes a phased array ultrasound transducer. The transducer includes a number of transducer elements that are electrically coupled to corresponding electrical conductors. In one embodiment, the conductors are included in a flex circuit and engage corresponding transducer elements though a conductive surface formed on outwardly extending ribs of a frame that holds the ultrasound array. In one embodiment, the phased array is forward facing in the medical device and has an element pitch of 0.75 lambda or less and more preferably 0.6 lambda or less. In one embodiment, the transducer is rotatable over an angle of +/−90 degrees to provide a 360 degree view of tissue surrounding the distal end of the device.

20 Claims, 14 Drawing Sheets

(51) Int. Cl.
  *A61B 8/08* (2006.01)
  *H01L 41/00* (2013.01)
  *B06B 1/06* (2006.01)

(52) U.S. Cl.
  CPC ........... *A61B 8/0891* (2013.01); *A61B 8/4488* (2013.01); *A61B 8/4494* (2013.01); *B06B 2201/76* (2013.01); *Y10T 29/42* (2015.01)

(56) References Cited

U.S. PATENT DOCUMENTS

| | | | |
|---|---|---|---|
| 5,957,850 A * | 9/1999 | Marian, Jr. | ........... B06B 1/0622 600/459 |
| 8,316,518 B2 | 11/2012 | Lukacs et al. | |
| 2009/0247879 A1 | 10/2009 | Angelsen et al. | |
| 2013/0140955 A1* | 6/2013 | Chaggares | ............. H05K 1/181 310/334 |
| 2014/0055007 A1* | 2/2014 | Gruhler | ................ G10K 11/004 310/348 |
| 2014/0114182 A1 | 4/2014 | Petersen et al. | |
| 2014/0350407 A1 | 11/2014 | Chaggares et al. | |
| 2016/0008850 A1 | 1/2016 | Kim et al. | |

FOREIGN PATENT DOCUMENTS

| | | |
|---|---|---|
| CN | 103811366 A | 5/2014 |
| JP | 2012-503370 A | 2/2012 |
| KR | 10-2014-0107894 B1 | 9/2014 |
| KR | 101484959 B1 | 1/2015 |
| WO | 2014139005 A1 | 9/2014 |
| WO | WO 2014/190326 A1 | 11/2014 |
| WO | 2017091633 A1 | 6/2017 |

OTHER PUBLICATIONS

Supplementary European Search Report dated Jun. 26, 2019 in Application No. EP 16869204.
Notice of Allowance dated Jan. 5, 2018 in Taiwan Application No. 105138791, 5 pages.
Bezanson et al. "Fabrication and Performance of a Miniaturized 64-Element High-Freiquency Endoscopic Phased Array," *IEEE Transactions on Ultrasonics, Ferroelectrics, and Frequency Control*, vol. 61, No. 1, Jan. 2014, pp. 33-43.

* cited by examiner

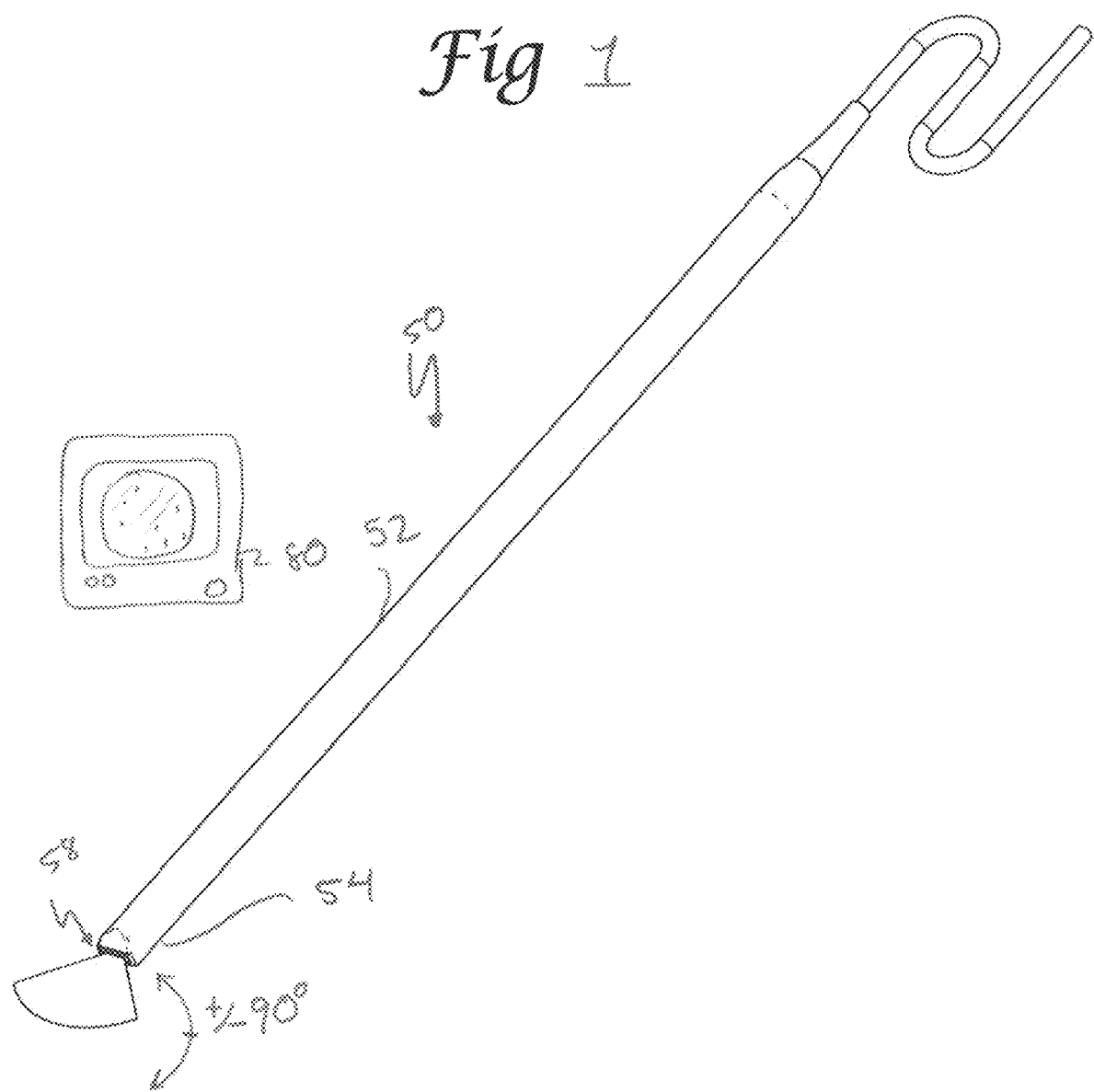

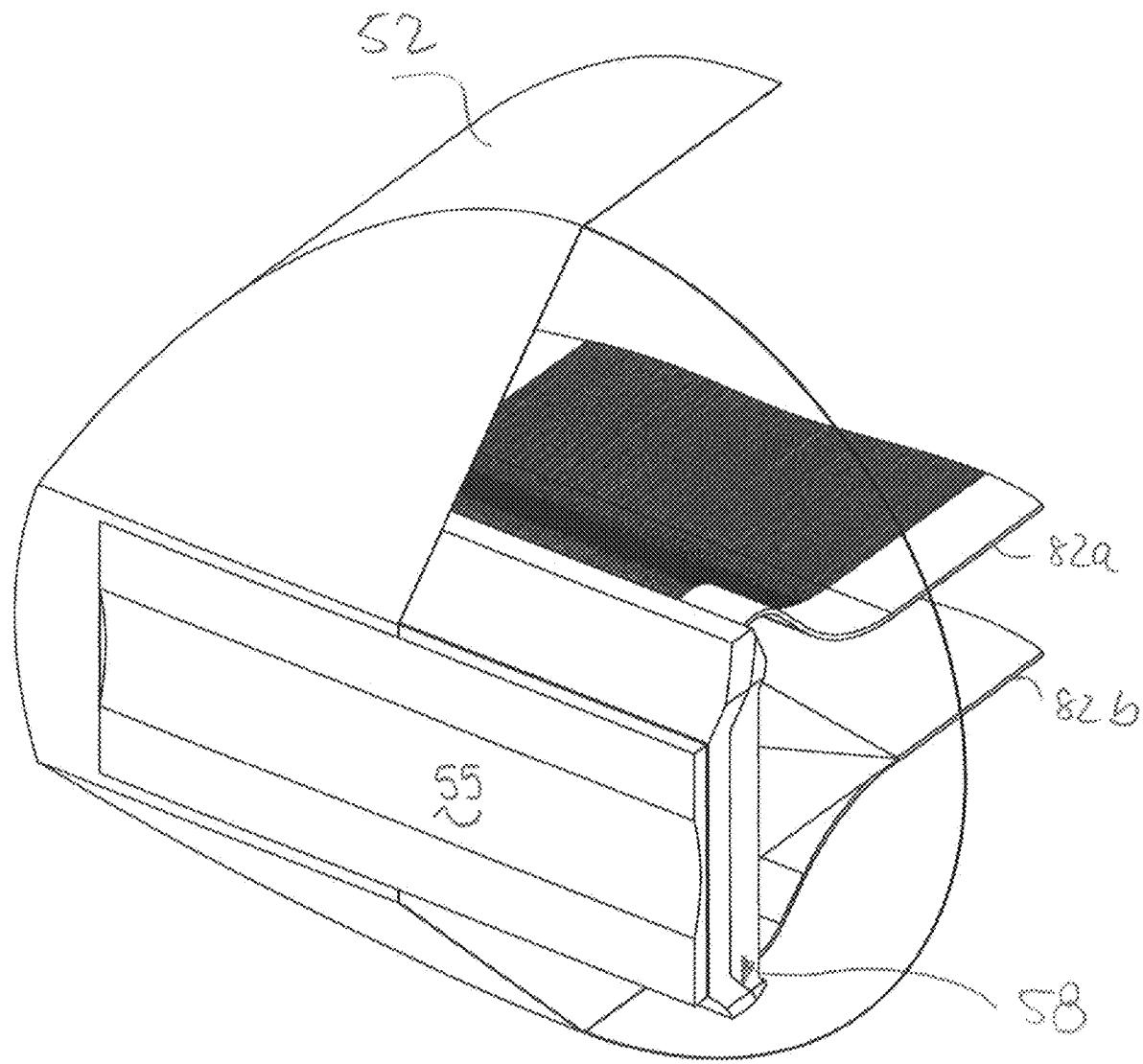

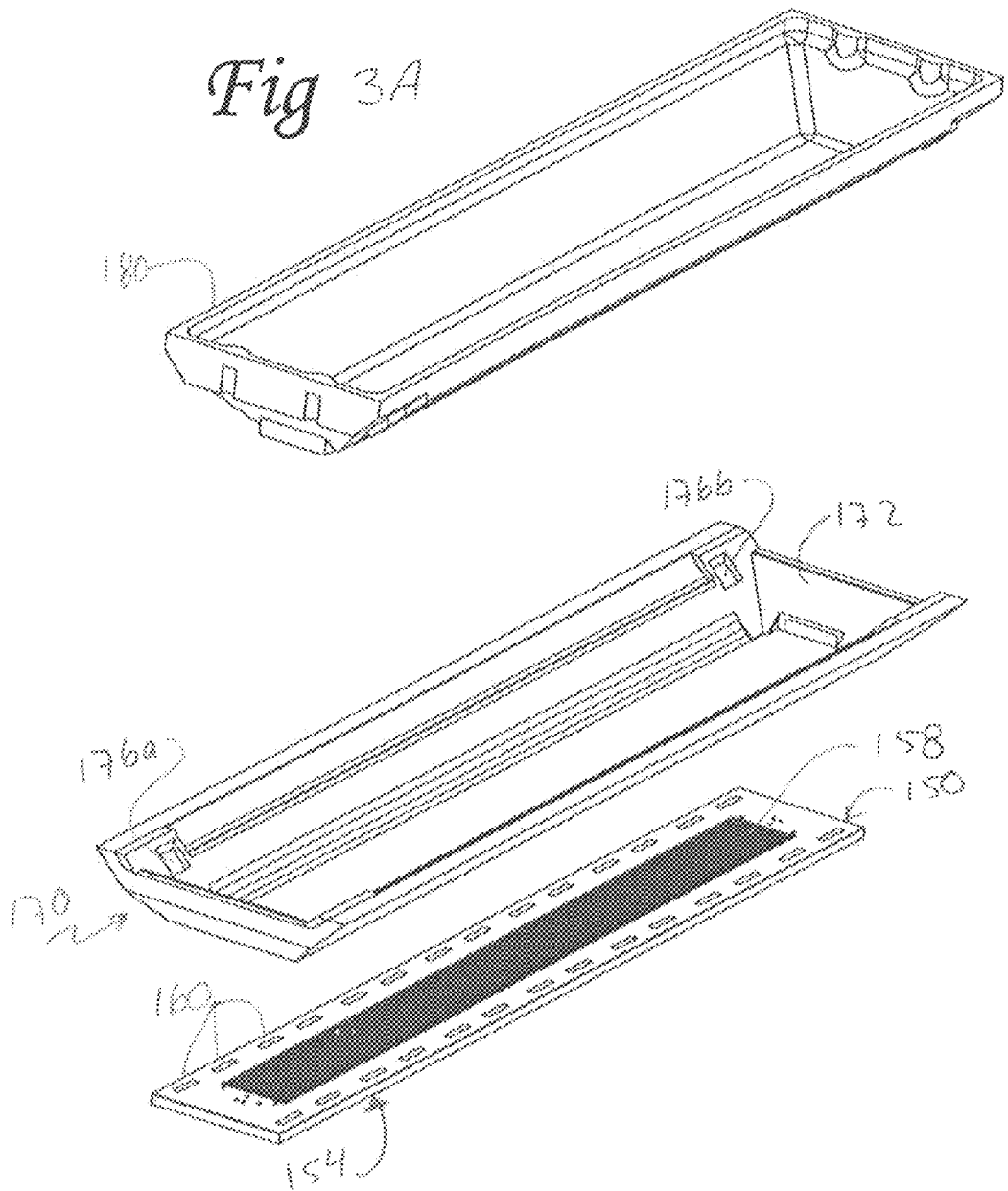

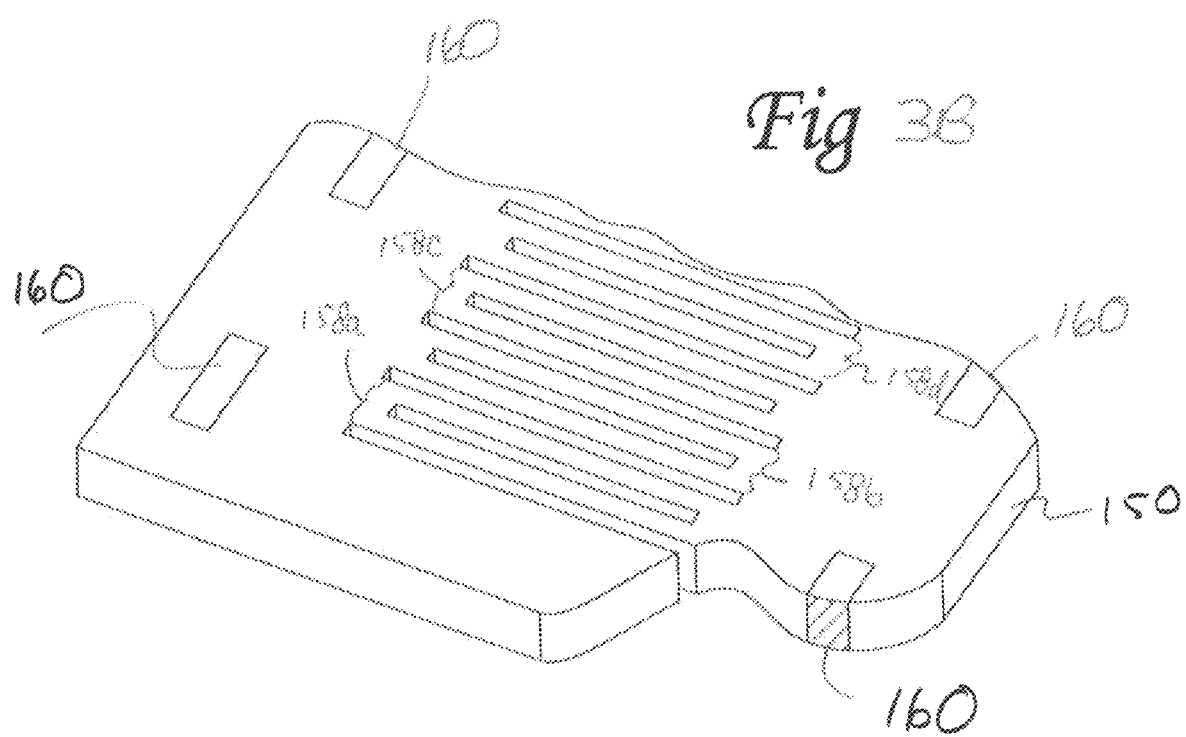

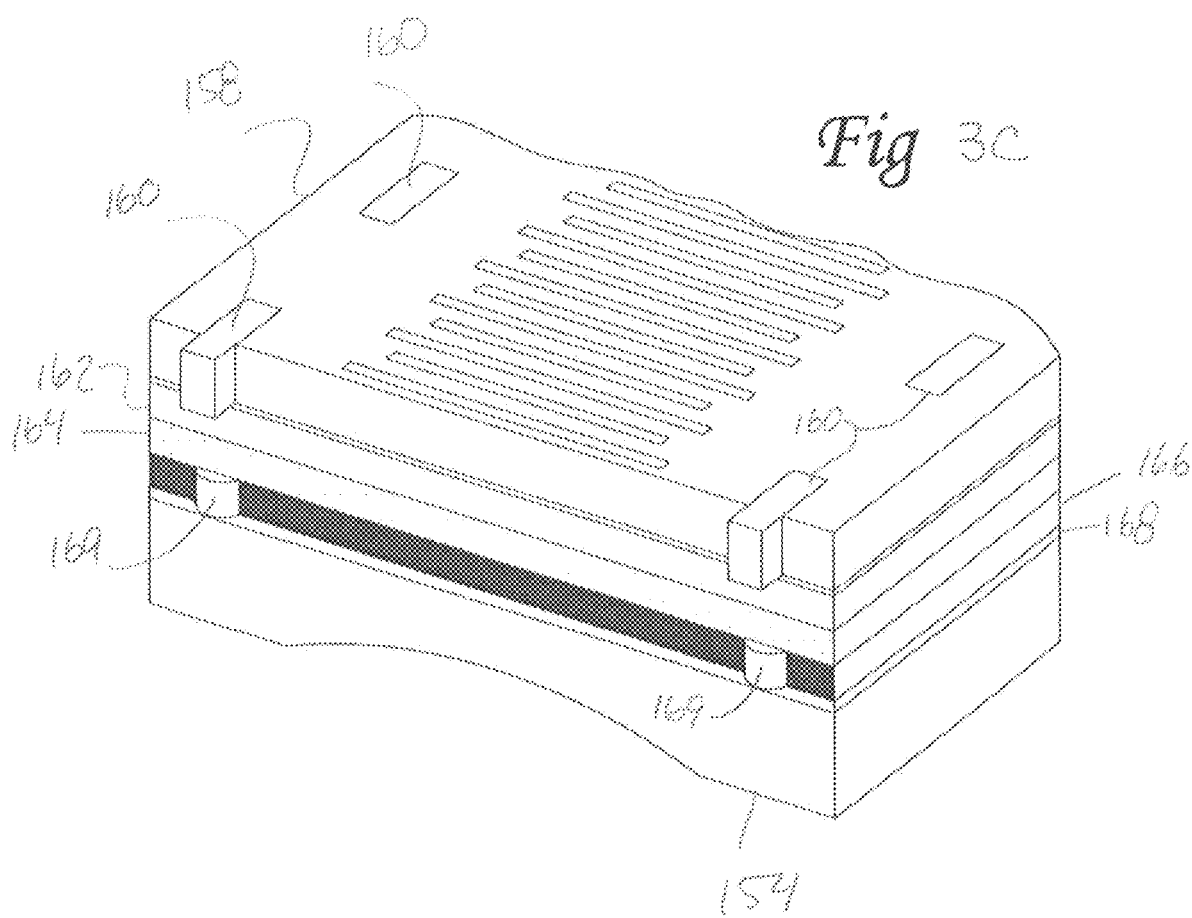

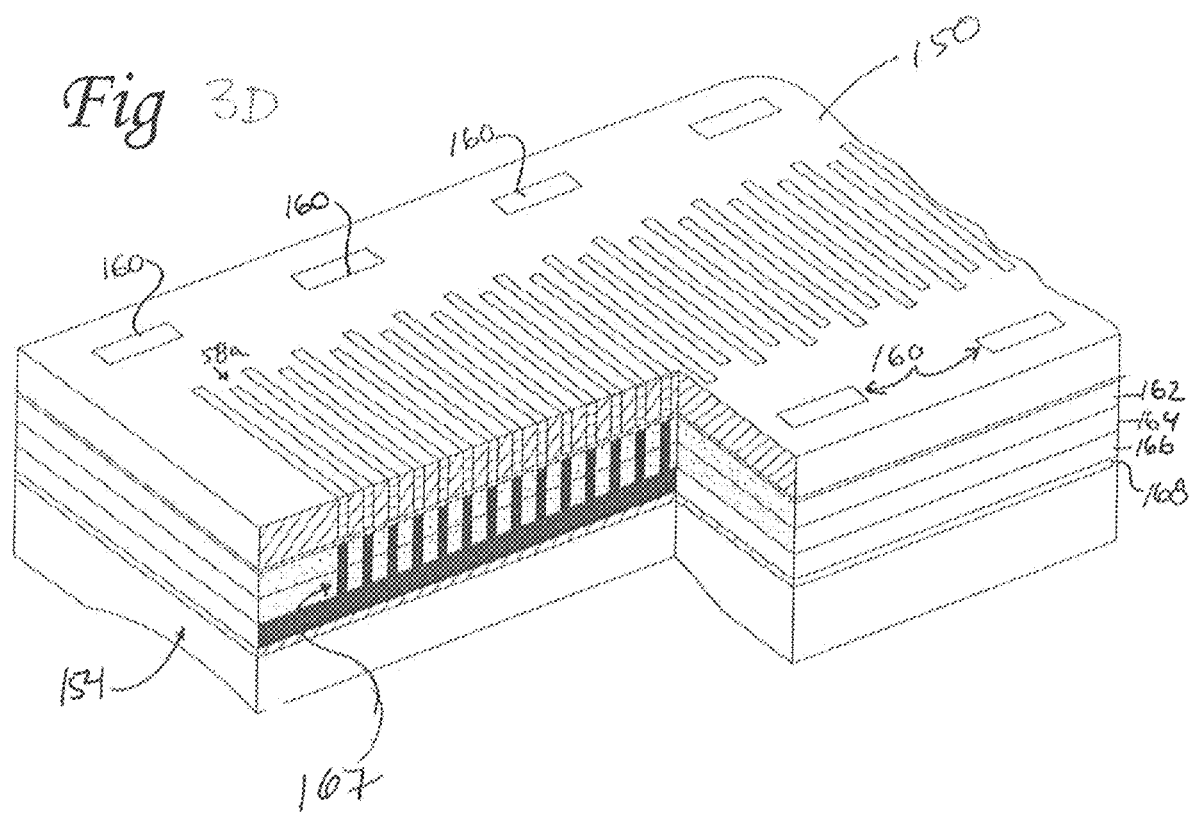

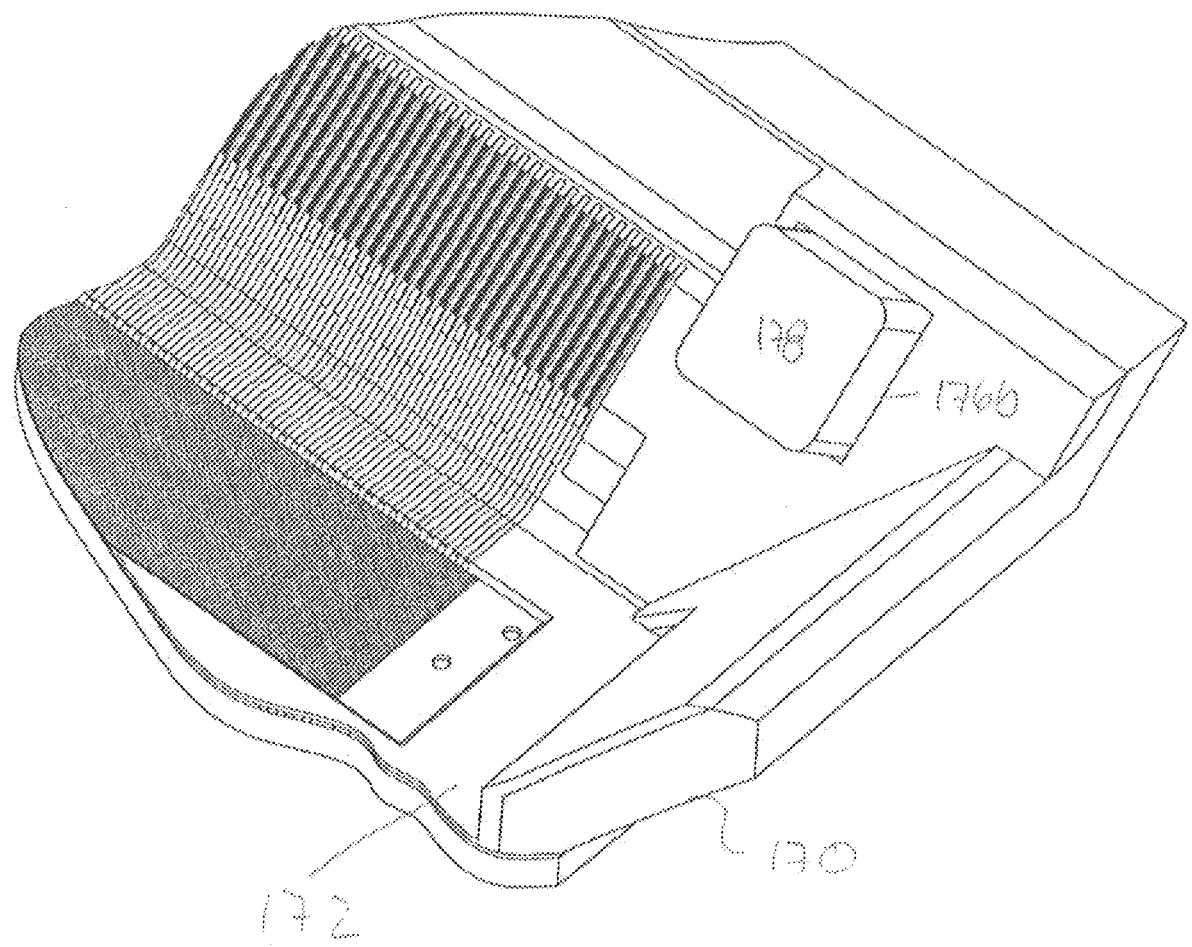

MEDICAL INSTRUMENT INCLUDING HIGH FREQUENCY ULTRASOUND TRANSDUCER ARRAY

RELATED APPLICATION

The present application claims the benefit of U.S. Provisional Application No. 62/260,219 filed Nov. 25, 2015, which is herein incorporated by reference in its entirety.

TECHNICAL FIELD

The disclosed technology relates to medical devices and in particular, to medical devices that include ultrasound transducers.

BACKGROUND

Ultrasound catheters are commonly used for in-vivo imaging of blood vessels and other tissues. In most cases ultrasound catheter type transducers, for example, IVUS transducers, operate at high frequencies (>15 MHz center frequency) making arrayed transducers difficult to make and electrical interconnection and packaging challenging in the tight confines of the catheter shaft. The absence of commercially available high frequency phased arrays (above 15 MHz center frequency) leave forward looking catheter-based ultrasound transducers reliant on mechanically scanned single element solutions, side looking linear arrays or ring arrays sometimes used in conjunction with a separate forward looking transducer. In most cases the maximum size of the catheter prohibits the use of conventional ultrasonic array technology and associated electrical interconnection techniques for endoscopic applications.

A typical ultrasound catheter includes a side-firing, single or multi-element array that is positioned at the distal end of a thin, steerable shaft. In some devices, a mechanism is connected to the transducer so that it can be rotated +/−180 degrees or a full 360 degrees to image tissue in all directions around the catheter. Such a mechanism often involves the use of one or more slip rings or other movable electrical connections. Problems with these types of catheters include the fact that the movable connections required for a single element transducer are often subject to failure and that a multi element ring array transducer cannot image tissue that is ahead of the catheter often requiring additional forward looking transducers to provide that function. Attempts to orient the transducer array in partially forward looking direction are often limited by the size of the cables or wires that connect to the individual transducer elements, and rely on mechanical scanning to produce complete images of the vessel walls circumference. In addition, high frequency curvilinear arrays are not commercially available in the small packages required for catheter based applications.

Given these problems there is a need for a mechanism for decreasing the size of the connections to a transducer array as well as the size of the array elements and interconnections so that it can be operated as a high frequency phased array oriented in a forward facing direction or for using a larger transducer in a side-firing orientation or partially side-firing direction (e.g. 45 degrees forward) while still allowing the catheter to have a diameter that is small enough to image small vessels or other tissues.

BRIEF DESCRIPTION OF THE FIGURES

FIG. 1 shows an ultrasound catheter in accordance with one embodiment of the disclosed technology;

FIG. 2A is a close up view of a forward facing ultrasound transducer that is positioned within a catheter in accordance with an embodiment of the disclosed technology;

FIG. 3A illustrates an array of ultrasound transducer elements and a conductive frame in accordance with an embodiment of the disclosed technology;

FIG. 3B illustrates an array of transducer elements in a sheet of piezoelectric material in accordance with an embodiment of the disclosed technology;

FIG. 3C illustrates an isometric, cross-sectional view of a portion of a transducer array, a stack of matching layers and a lens element in accordance with an embodiment of the disclosed technology;

FIG. 3D illustrates an isometric, cross-sectional view of a portion of a transducer array, a stack of matching layers and a lens element in accordance with an embodiment of the disclosed technology;

FIG. 4 shows a close up view of a corner of the conductive transducer frame and a registration feature in accordance with an embodiment of the disclosed technology;

DETAILED DESCRIPTION

Figure 2B:
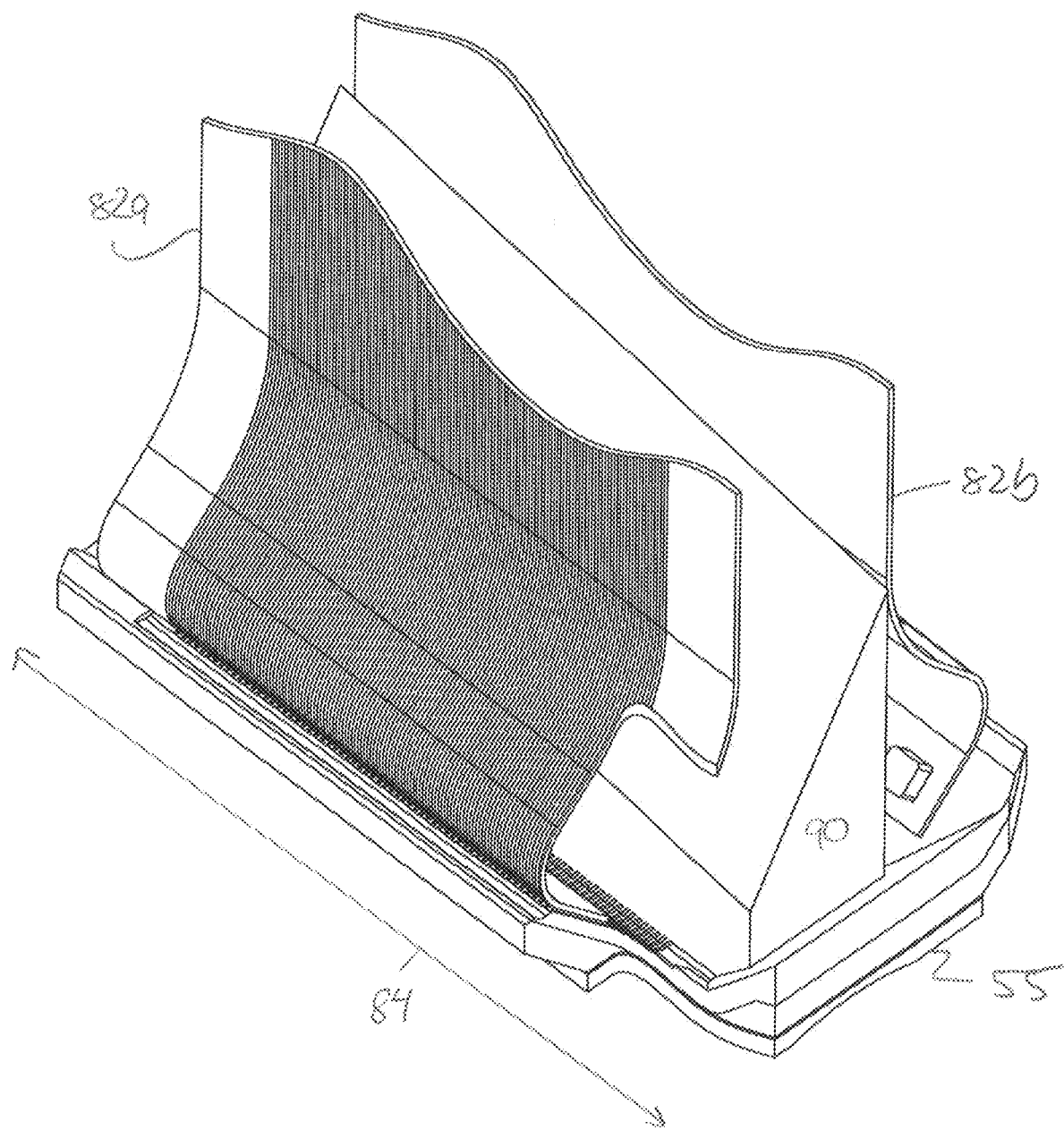
FIG. 2B illustrates how traces in a pair of flex circuits are connected to an array of transducer elements in accordance with an embodiment of the disclosed technology.

FIG. 1 illustrates an ultrasound catheter constructed in accordance with one embodiment of the disclosed technology. In the embodiment shown, the catheter 50 includes a flexible shaft 52 having a distal end 54 and a proximal end. At the distal end of the shaft is a forward facing, ultrasound phased transducer array 58 that is positioned behind a polymeric lens 55 (FIG. 2A) such as Rexolite™ polystyrene or TPX™ polymethylpentene. The flexible shaft 52 may also include one or more lumens (not shown) for the passage of guidewires or other medical devices. In one embodiment, the shaft 52 includes a number of control wires (not shown) that can be used to orient the distal end of the shaft in a desired direction.

In the embodiment shown, the proximal end of the catheter 50 includes an electrical connector (not shown) at which electrical signals can be supplied to or received from the catheter. In some embodiments the catheter may include a handle with a manual or electronic control mechanism that operates to rotate the orientation of the transducer array 58 over an angle of +/−90 degrees. In one embodiment, the control mechanism 64 can include an elastomeric or metal sleeve that is connected to the ultrasound transducer array 58 and through which electrical conductors to the transducer elements are routed. Rotation of the proximal end of the sleeve in the handle of the catheter operates to rotate the transducer array 58 at the distal end of the catheter. As will be appreciated by those of ordinary skill in the art, other mechanisms for rotating the orientation of the transducer array 58 are also possible. Because the transducer is only rotated over a range of +/−90 degrees, movable connections or joints are not required. For example, the entire catheter length can be rotated back and forth over an angle of +/−90 degrees by simply rotating the proximal end. Because the beams of transducer can be electronically steered to image the walls of a vessel in which the catheter is located, rotation of the catheter in the vessel or other organ allows the transducer to obtain a full 360 degree view of the tissue ahead of the transducer.

Signals produced by the ultrasound transducer array 58 are processed in a conventional fashion and displayed on a monitor 80 or stored on a computer readable medium for later retrieval or analysis. Because the ultrasonic transducer array 58 is forward facing, the operator has a better view of the vessel or tissue in which the catheter is located, thereby facilitating advancement of the device into the body.

FIG. 2A shows a number of conductors that are connected to each of the individual elements in the transducer array 58. In one embodiment, the transducer array 58 is connected to one or more flex circuits 82a, 82b. Flex circuit 82a has a number of traces therein that connect to the even numbered transducer elements, while flex circuit 82b has traces that are connected to the odd numbered transducer elements of the transducer array. In another embodiment, a single flex circuit that is connected to one side of the transducer includes traces that are connected to each of the transducer elements. In one embodiment, the transducer array 58 has 64, 96, 128 (or more) elements at a pitch of about 15-45 μm. With the pitch of transducer elements being less than 0.6 lambda and more preferably around 0.5 lambda (e.g. the wavelength of the ultrasound signals transmitted), the transducer array can operate as a phased array with beamforming directions that extend over a range of, for example, +/−45 degrees. At 15-60+ MHz., the echo signals created by the transducer elements allow fine details of the region of interest to be seen.

In one embodiment, using the techniques described herein, it is expected that a 64 element transducer array having an operating frequency of 50 MHz with an element pitch of 15 microns can be made to fit within a catheter or probe that is approximately 2-3 mm. in diameter. This allows the probe to be inserted into small body cavities including blood or other vessels. Ultrasound imaging arrays with other operating frequencies for example, 15-60 MHz and higher as well as with different numbers of array elements (e.g. 128, 256, 512 or others) can also be manufactured using the techniques described herein. For one example, a 128 element 15 MHz phased array transducer can be made to fit in probe of approximately 8 mm. in diameter. In a second example, a 64 element 40 MHz phased array transducer can be made to fit in a probe of approximately 2 mm in diameter. Other combinations are also possible.

As will be appreciated, the probe need not be always be flexible. For example, rigid or semi-rigid probes having ultrasound imaging arrays may be used to image surgical procedures or to image internal body tissues. The probe can be straight, can have pre-defined shapes or can be moldable to have a shape selected to image particular body tissues. Probes with fewer elements can be made even smaller at the same pitch or larger arrays can be used where the diameter of the catheter can be larger. In some embodiments, the orientation of the ultrasound transducer may be fixed in the probe and require the operator to move or rotate the probe in order to image additional areas of body tissues. In yet another embodiment, the phased array transducer is not oriented directly in a forward facing direction but is oriented at an angle, such as 45 degrees, to the front face of the probe. In yet another embodiment, the transducer array 58 can be side firing in the catheter.

In one embodiment, the one or more flex circuits 82a, 82b are twisted around the longitudinal axis of the catheter shaft as they extend up the length of the catheter. This allows the distal tip of the catheter to be oriented in any direction rather than being flexible in one plane and stiff in another.

As discussed above, one of the challenges associated with fitting a catheter with a forward facing ultrasound transducer array is being able to connect the transducer elements with a number of traces that are not significantly larger or wider than the transducer itself. If the transducer elements are connected to conductors in a flex circuit that is much wider than the transducer itself, then the array cannot be inserted into a catheter that is thin enough to be inserted into a region of interest. In one embodiment of the disclosed technology, a narrow flex circuit 82 containing the traces can be formed by printing the traces using photolithographic techniques. However, the traces need to be accurately placed on the transducer so that the traces align with the individual transducer elements.

In the past, the conductive traces had to be aligned with the transducer elements by hand and then carefully handled until the fabrication process was completed. If the transducer assembly was accidentally bumped or the traces were not correctly aligned, the result was a rejected part. This problem is even more acute as the operating frequency of the ultrasound transducer increases and the transducer elements become even smaller. The technology described herein simplifies the manufacturing process steps of creating an ultrasound transducer with minimal width.

As shown in FIG. 2B, the transducer has a frame with a dimension 84 that is greater (e.g. wider) than the width of the of the flex circuits 82 that carry signals to and from the elements of the transducer array. In FIG. 2B, a corner of the transducer is shown cut away so that the connection between the ribs of the transducer array can be seen where they connect to the exposed portions of the traces on the flex circuits 82 as will be explained in detail below. A backing member 90 is placed over the proximal side of the array elements to absorb and/or reflect ultrasound signals radiating from the rear surface of the array.

FIGS. 3A-3D and the description below provide a brief overview of a number of steps performed when manufacturing a high frequency ultrasound transducer in accordance with some aspects of the disclosed technology. Additional details of some aspects of the manufacturing processes can be found in U.S. Patent Publication Nos US 2013/0207519; US 2013/0140955; US 2014/0350407; and US 2015/0173625, all of which are commonly assigned to Fujifilm SonoSite Inc., the assignee of the present application and are herein incorporated by reference in their entirety. In one embodiment, a rectangular sheet of piezoelectric material 150 is mounted to a flat manufacturing puck with the lower surface facing up and is then machined with a patterning tool such as an excimer laser. The laser or other patterning tool is then used to create an array of individual transducer elements 158 and to create a number of vias 160 that are spaced around the perimeter of the transducer array. As shown in FIG. 3B, an array includes a number of transducer elements 158a, 158b, 158c etc. In one embodiment, each transducer element 158 is sub-diced in the center of each element along its length to prevent vibration in undesired modes. In the embodiment shown, the kerf slots that define the array elements and the sub-dices are shown having a length that is less than the width of the piezoelectric material. However, it is also possible to run the kerfs out to the edges of the piezoelectric material 150.

The spaces between the transducer elements and in the sub-diced kerf slots are filled with a suitable acoustically soft material such as, for example, a soft epoxy using a vacuum pressure impregnation technique. After filling the kerfs, the surface is lapped or ground flat just to the surface of the piezoelectric material and is then sputter coated with a conductive metal such as gold or chromium plus gold that forms a ground conductor on the lower surface or front face of the transducer. The vias 160 are filled with a conductive epoxy covering and filling the plated via holes. With the vias now plated and filled, the vias 160 form electrically conductive paths to the conductor on the front face of the transducer array. In operation, the conductor on the lower surface of the transducer is typically connected to a common ground while a driving signal is applied to the top surface of a selected transducer element by a conductive lead (not shown). The selected transducer element vibrates to produce an acoustic ultrasound signal. During a receive cycle, acoustic energy impinges on the transducer elements and creates signals on the leads that are read by signal processing circuitry (not shown).

As shown in FIGS. 3C and 3D, the front face of the transducer is connected to a lens material 154 through a number of matching layers. In one embodiment, two powder-filled epoxy matching layers 162 and 164 are applied to the gold coated surface of the piezoelectric material 150, each forming a part of a four layer matching layer system. Each of the layers 162 and 164 is lapped after it is applied to ensure the proper thickness of the layer. As shown in FIG. 3D, kerfs 167 are placed in the matching layers 162, 164 in areas that correspond to the spaces between the transducer elements. The kerfs 167 are filled with the adhesive that is used to bond the lens 154 to the matching layer 164.

A lens 154 is then bonded to the outer surface of the matching layer 164 using an adhesive 166. In one embodiment, the lens 154 is made of a polymer such as Rexolite™ polystyrene or TPX™ polymethylpentene. However, other lens materials could be used. In one embodiment, the lens 154 is coated with a layer of adhesive such as cyanoacrylate (CA) glue 168 that is capable of adhering to the special lens material. The CA glue can adhere to the lens surface and can be adhered to by other adhesives more generally useful for creating acoustic matching layers.

The layer of cyanoacrylate is lapped to a thickness suitable for acting as an acoustic matching layer at the frequency of the array, for example, a quarter wave matching layer. The outer surface of the CA glue layer is then bonded to the outer surface of the matching layer 164 with an adhesive 166 such as a powder filled epoxy that adheres to the cyanoacrylate coated lens material 54. The adhesive 166 forms the third quarter wave matching layer of the four layer system, with the CA layer 168 forming the $4^{th}$ of four layers. The adhesive 166 is applied under vacuum to remove any air in the kerfs 167. In one embodiment, the composition of the matching layers 162, 164, 166 is described in commonly assigned U.S. Pat. Nos. 7,750,536 and 8,343,289, which are herein incorporated by reference in their entirety.

In one embodiment, the thickness of the adhesive 166 required to create the third matching layer is controlled by placing a number of spacing elements 169 around the lower perimeter of the sheet of piezoelectric material 150. The spacing elements 169 are lapped to a desired thickness to form pillars with a height that is selected so that the adhesive 166 forms the quarter wave matching layer. As best shown in FIG. 3C, with the spacing elements 169 in place, the adhesive 166 is placed over the matching layers already applied to the surface of the piezoelectric sheet and the CA coated lens material 154 is pressed against the spacers 169 to bond the lens material at the desired distance from the surface of the uppermost matching layer previously applied to the plated piezoelectric material 150.

The sheet of piezoelectric material 150, the acoustic matching layers 162, 164, 166 and 168 and the lens 154 are then mounted lens-side down to a manufacturing puck and lapped on the exposed piezoelectric side so that the transducer elements have a desired thickness.

A conductive metal frame 170 shown in FIG. 3A, that is made molybdenum or a like metal is bonded to the upper surface of the transducer array with a conductive epoxy. The conductive frame is therefore electrically connected to the conductive material on the front surface of the transducer array through the conductive paths created by the filled vias 160. The frame 170 has an open bottom surface so that an upper surface of the transducer elements is accessible through the opening in the bottom of the frame 170. The frame 170 has sloped side walls that together form a trough over the array of elements 158. Although the disclosed embodiments utilize a conductive frame, it will be appreciated that a non-conductive frame could also be used and connections to the electrode on the distal side of the transducer could be made with a conductive foil, wires or other electrical conductors.

Once the frame 170 is bonded to the transducer array, a cover is placed over the transducer elements and a powder-filled epoxy 172 material is added to an open side of the frame 170. In one embodiment, the powder added to the matrix material is powdered silica that adds texture to the surface of the epoxy after laser machining. A mold 180 that is covered with a release agent is then pressed into the epoxy 172 while it cures to create a number of desired feature shapes in the frame. In one embodiment, the shapes may include a pair of recesses 176a, 176b that are located on a sidewall of the frame at a location beyond the ends of the ultrasound array. Additional recesses may be formed on the opposite sidewall of the frame (not shown).

FIG. 4 shows a close up view of one corner of the frame 170 and a recess 176b that is formed in the epoxy 172. A registration feature 178 is placed in each of the recesses 176 and is used to align the electrical traces of a flex circuit to the transducer elements as will be described below. In one embodiment, the registration feature is preferably made of a molded powder-filled epoxy material and is precisely laser machined to a tolerance of, for example, +/−5 microns. The registration features 178 can be secured within the recesses 176 with an adhesive. In some embodiments, an undersized recess 76 can be molded into the epoxy and trimmed to size with a laser or other micro-machining tool to accurately position the recess with the position of the ribs. With the recess accurately positioned and trimmed, a registration feature 78 is glued into the recess in order to fit with a corresponding alignment feature on the flex circuit. In some other embodiments, a blob of excess epoxy or the other glue can be placed on the frame and micro-machined with a laser or the like into a registration feature. The registration feature(s) on the frame and the corresponding alignment features on the flex circuits allow the exposed traces of the flex circuits to line up with the conductive ribs on the frame.

The powder-filled epoxy 172 in the transducer frame 170 is then machined using the excimer laser to create a number of channels that extend partially up the side walls of the frame and connect to the individual transducer elements of the transducer array. In the past, flex circuits were secured to the frame 170 before the powder-filled epoxy was added to the frame in order to cover the exposed circuit traces with epoxy. A patterning tool such as the excimer laser would then be used to tunnel through the epoxy to expose a portion of a circuit trace on the flex circuit. While this worked well, the traces on the flex circuits were aligned with the transducer elements by hand before being fixed to the frame. In addition, the assembly was delicate until the transducer could be potted in a material that holds the flex circuits and transducer assembly together.

Figure 5:
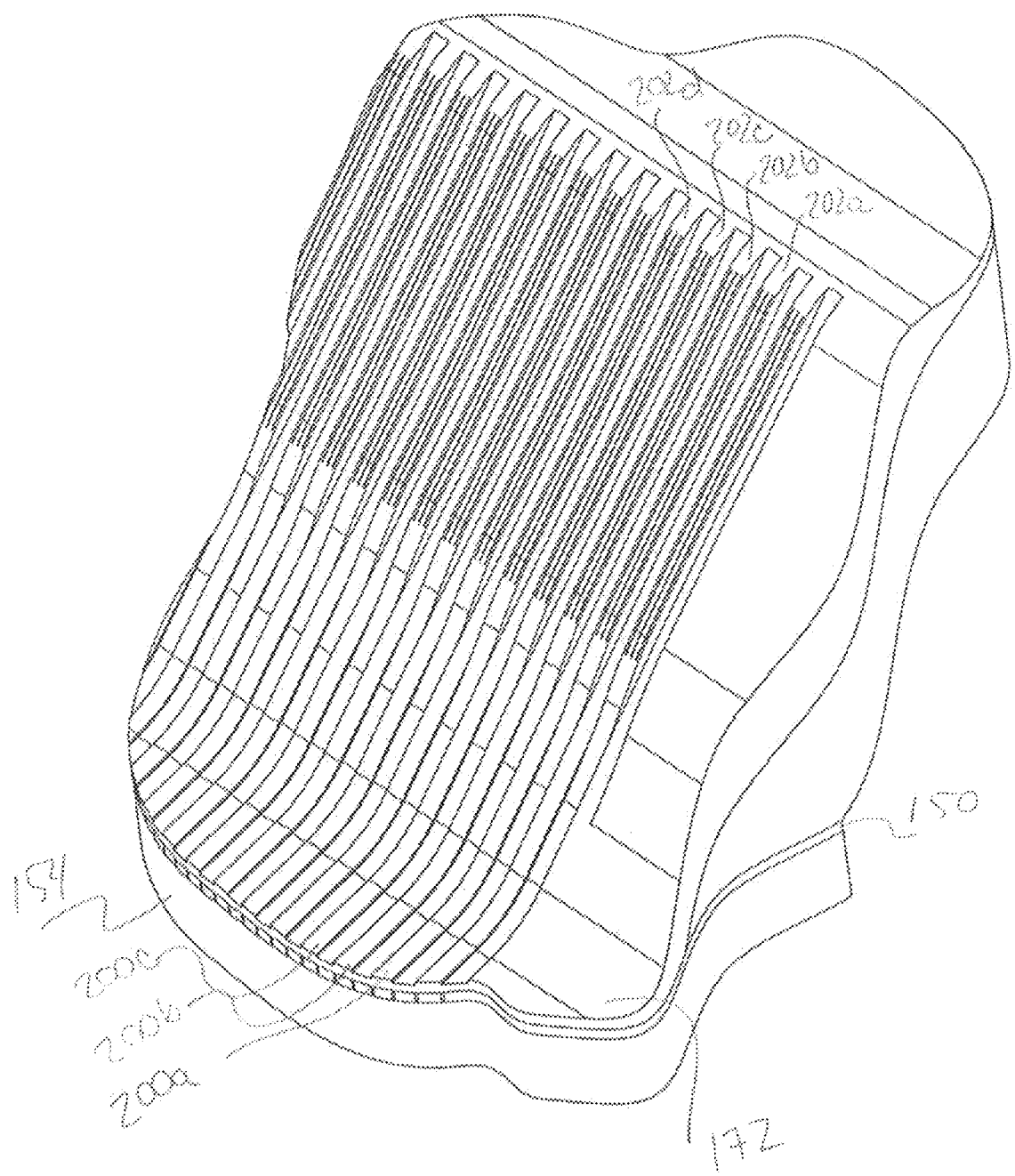
FIG. 5 shows a close up view of a number of outwardly extending ribs formed on the frame that are configured to engage electrical traces on a flex circuit in accordance with an embodiment of the disclosed technology.

To improve on this assembly technique, the channels that connect each transducer element to a trace are fashioned so that each channel becomes a raised rib as it extends up the sidewall of the frame 170. As can be seen in FIG. 5, a number of channels 200a, 200b and 200c etc., are cut into the powder-filled epoxy 172 at a pitch that equals the pitch of every other transducer element (e.g. all the odd numbered transducer elements) while interleaving channels are created on the other side of the frame that are aligned with all the even numbered transducer elements. Alternatively, channels can be created on only one side of the frame that align with each transducer element. In one embodiment, the channels that are aligned with each of the transducer elements have a depth that decreases as the channel extends outwardly from the transducer element. About half way up the sidewalls of the frame 170, the depth the channel is reduced to a point where the "channel" begins to extend outwardly from the surface of the epoxy to form an outwardly extending rib 202a, 202b and 202c etc. In one embodiment, the ribs 202 are created by ablating the powder-filled epoxy 172 on either side of the areas that defines the ribs. In one embodiment, a number of score lines are created with the laser along the top surface of each rib 202 to increase the surface area on top of the ribs 202 and to ensure robustness of a gold electrode during the pressing that takes place as part of the fixturing of a flex circuit to the conductive surface of the raised ribs.

Once the channels and the ribs and are patterned into the epoxy, the top surface of the transducer assembly is plated with a conductor such as gold or gold plus chromium and processed to leave a conductive layer in the channels 200 and on top of the ribs 202. In one embodiment, the conductive material is applied by sputter coating a layer of metal such as gold or gold plus chromium on the surface of the transducer array including the top surface the transducer elements and the ribs. Next, a resist layer is applied over the transducer and exposed in areas where the conductive material is to be removed using photolithographic techniques. In one embodiment, the conductive material is to be removed from areas between the transducer elements, between the channel regions of the conductive paths, and should be removed from each side of the ribs. A chemical etch material is used to remove the resist and the conductive material from areas where it is not wanted. Finally, a laser is used to remove any traces of conductive material that remain after the etch process.

After the laser-etch-laser (LEL) process, there is a conductive path created between the top surface of each transducer element and a corresponding rib 202 on the frame 170. A flex circuit with a number of exposed traces is then fixed to the frame so that the exposed traces align with and engage corresponding ribs on the frame in order to create an electrical connection between the traces and the transducer elements. One of the benefits of this approach is that the flex circuits do not need to be secured to the transducer assembly while the top surface of the transducer is being coated with a conductive material. Therefore, there is less likelihood that the flex circuit connections will be broken during handling of the transducer. In addition, it is possible to fit more transducer assemblies into a sputtering machine chamber because the flex circuits are not yet attached while the coating is being applied. Therefore, more transducer assemblies can be processed at one time.

In the embodiment shown in FIG. 5, each of the ribs 202 terminates at the same height on the frame wall of the transducer. In another embodiment, the ribs 202 can terminate at different heights to allow interleaved traces to be connected to the ribs. For example, if the connections to be made to the transducer elements are smaller than the distance between the traces, the traces can be staggered or interleaved. One set of traces e.g. traces 1, 3, 5 etc. can be placed in one layer of a flex circuit and traces 2, 4, 6 etc. can be placed in a different layer of the flex circuit that is set back from the exposed traces in the first layer. The exposed portions of the traces in each layer can be bonded to the ribs that extend to different heights on the wall of the transducer frame. A similar technique for interleaving traces is disclosed in published U.S. patent application US 2013-0140955 A1 referenced above, and is incorporated by reference in its entirety.

Figure 9:
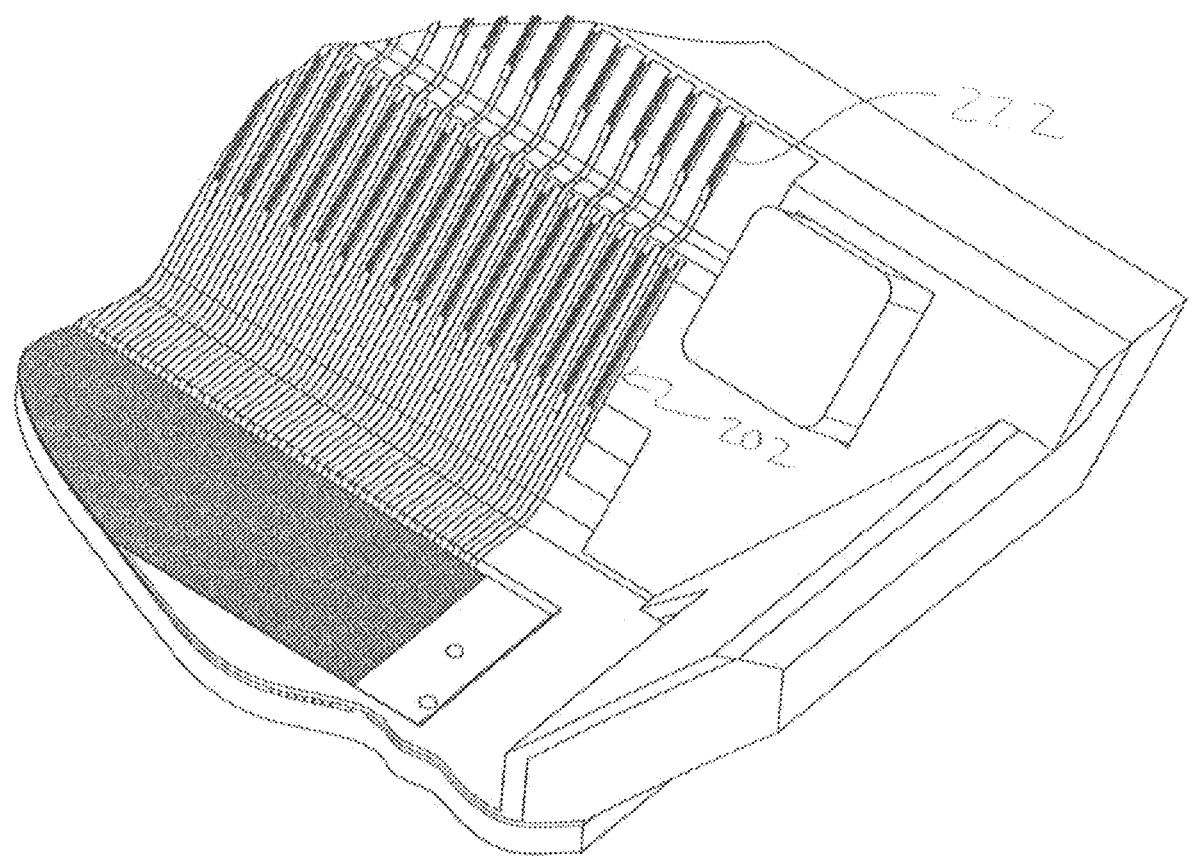
FIG. 9 shows a transducer having two rows of interleaving ribs that connect to individual transducer elements in accordance with another embodiment of the disclosed technology.

FIG. 9 shows an example of a portion of a ultrasound transducer having two sets of ribs at different levels. In the example shown, a frame includes a first set of ribs 202 that extends part way up the side wall of the transducer frame while a second layer of ribs 222 extends higher up the side wall of the transducer frame. The ribs on each level are interleaved.

One flex circuit (not shown) having exposed traces engages the ribs 202 while another flex circuit (also not shown) having exposed traces engages the ribs 222. As will be appreciated, it is possible to have more than two layers of ribs formed in the epoxy material if desired.

Figure 10:
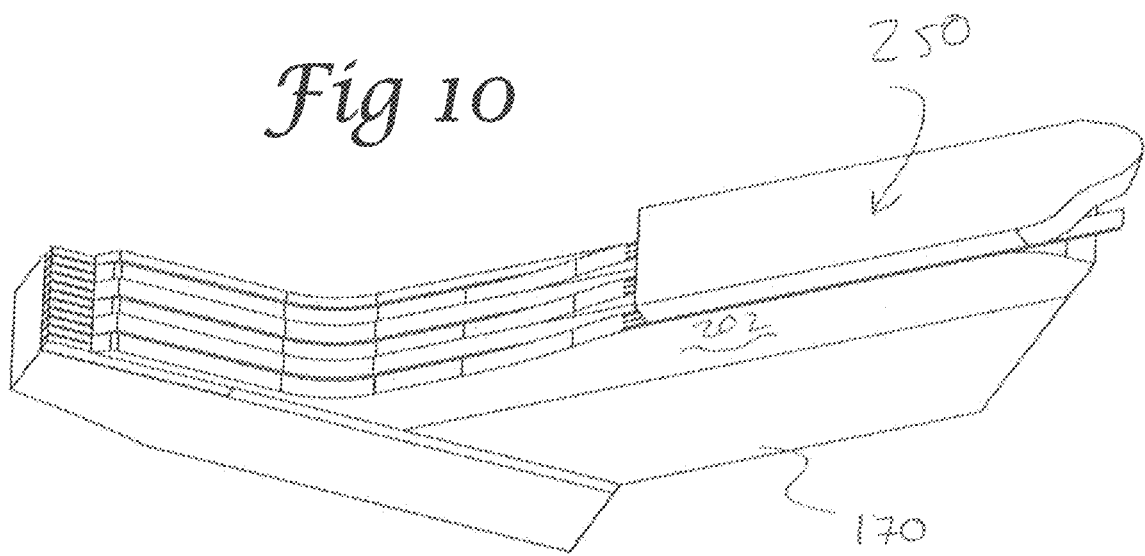
FIG. 10 shows an ultrasound transducer with a flex circuit having traces that are electrically connected to the elements of a transducer array in accordance with an embodiment of the disclosed technology.

In one embodiment, the exposed traces on the flex circuits are bonded to the conductive coating on the ribs 202 with a non-conductive adhesive. Because the laser machined surface of the power-filled epoxy is rough (on a microscopic scale), the coated particles of the filler material on top of the ribs act as conductive spikes that pierce through the adhesive and engage the conductors of the flex circuit when the flex circuit and the ribs are bonded together. FIG. 10 shows an example of a portion of a flex circuit 250 that is secured against the ribs 202 on the metal transducer frame. 170. Exposed portions of the traces (not shown) on the underside are pressed against the conductive coating on the ribs 202 and held in place with an adhesive in order to create an electrical connection with a corresponding transducer element in the transducer array. One or more ground connections of the flex circuit are connected to the metal transducer frame 170 of the transducer assembly (and therefor to the conductive coating on the front surface of the transducer array by the conductive vias) with a conductive epoxy.

Figure 6:
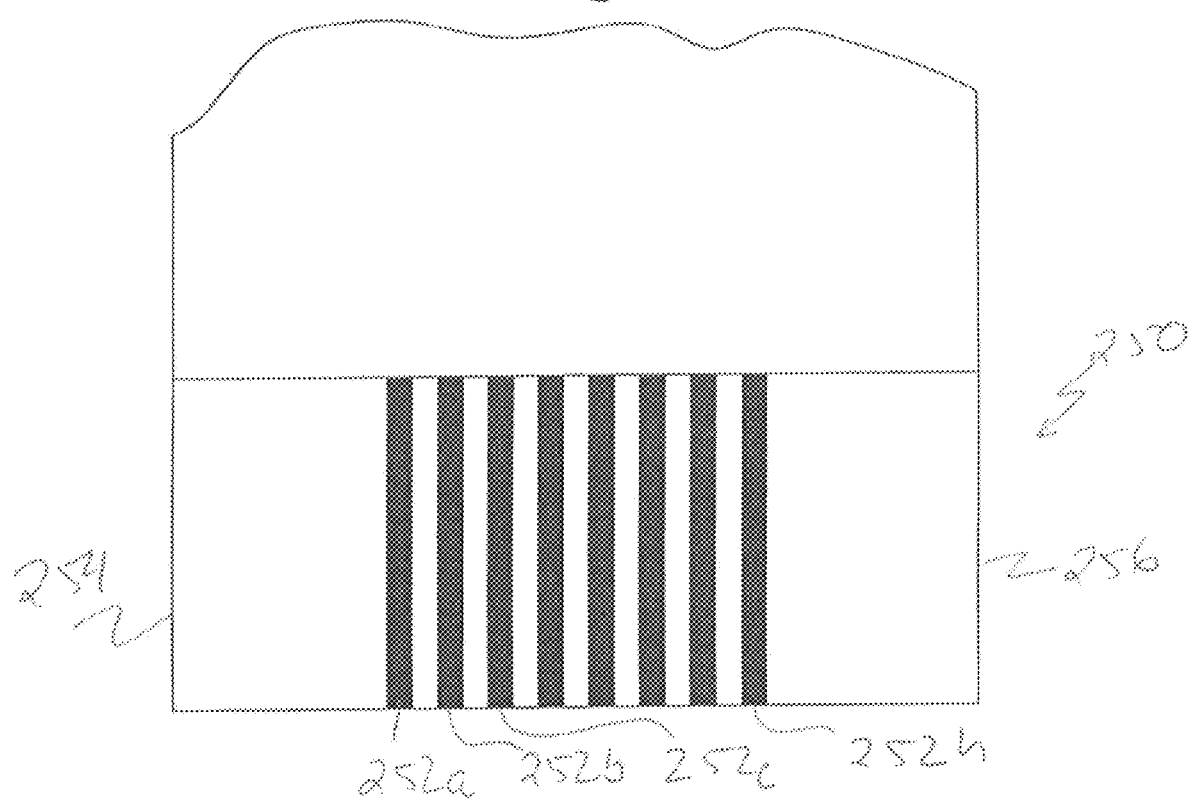
FIG. 6 shows a simplified flex circuit including a number of exposed traces.

Although manufacturers of flex circuits can create traces at a desired pitch with a high degree of accuracy, they often cannot control the distance between the edge of the flex circuit and the beginning of the traces with the same tolerances. There can be large variations in the distances between an edge of the flex circuit and a point where the traces begin. Therefore, it is not possible to simply align an edge of the flex circuit with a feature on the transducer frame and expect that the traces will align with conductors that are connected to the transducer elements. FIG. 6 shows a representative flex circuit 250 including a number of conductive exposed traces 252a, 252b, 252c . . . 252h. The distances between the traces 252 are often very accurate. However, the distance between an edge 254 and the nearest trace 252a or between an edge 256 and the nearest trace 252h can vary significantly between different flex circuits. To address this problem, the registration feature 178 shown in FIG. 4 is used.

Figure 7:
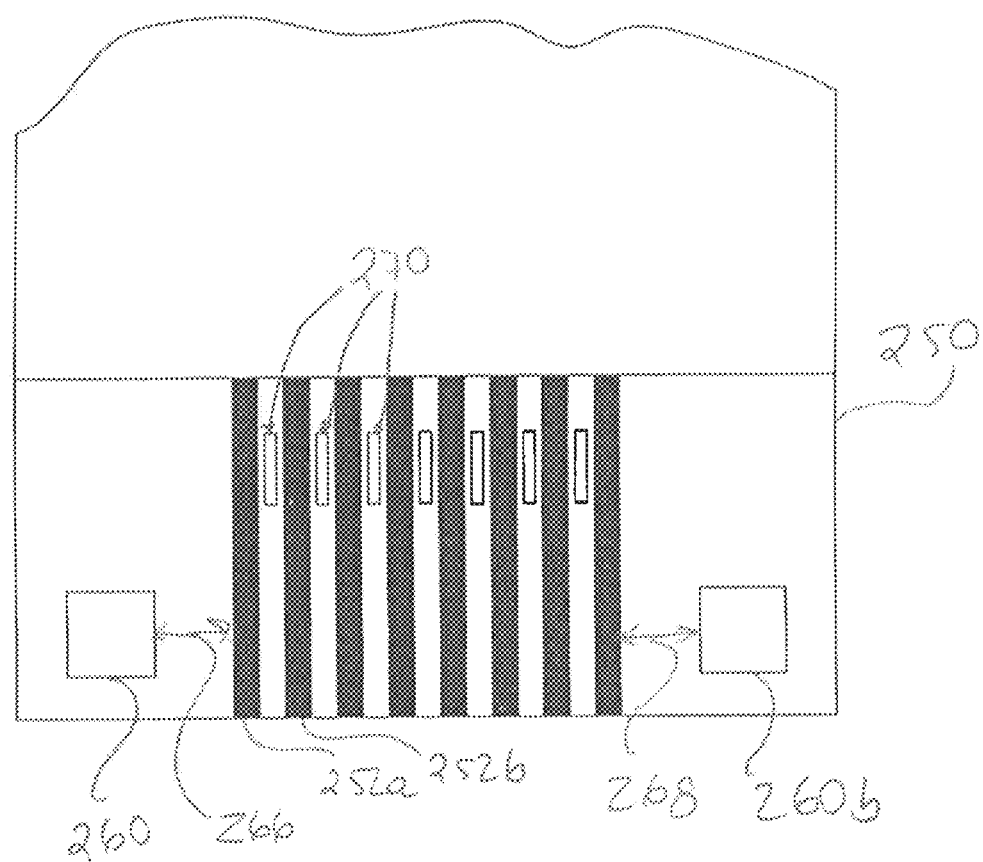
FIG. 7 shows a flex circuit including a pair of alignment features that allow the traces to be aligned with conductors connected to the transducer elements in accordance with an embodiment of the disclosed technology.

As shown in FIG. 7, one embodiment of the disclosed technology places alignment holes or features 260a, 260b in the flex circuit. Such features can be created with a laser at a predetermined distance 266, 268 from a reference point such as the nearest trace. As will be appreciated, the alignment holes 260 are designed to fit over the corresponding registration features 178 that are placed on the frame 170 so that when the registration features 178 are placed in the alignment holes 260, the traces on the flex circuit will align with the corresponding ribs on the frame.

Figure 8:
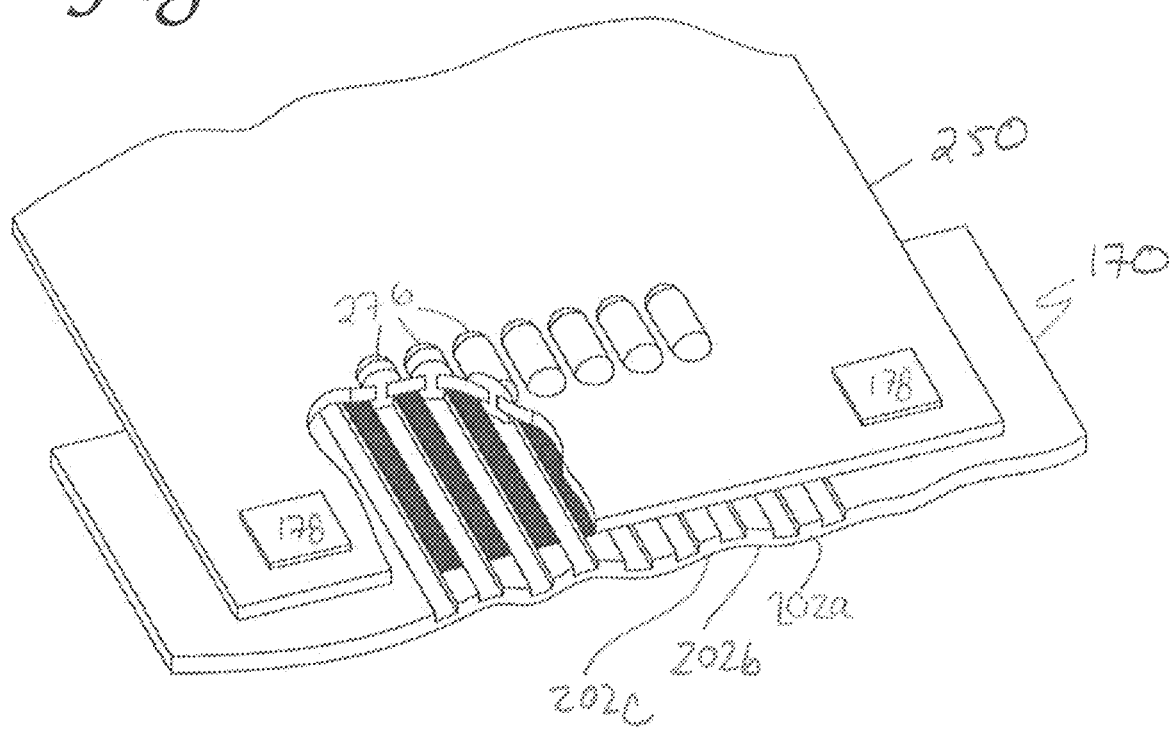
FIG. 8 shows a flex circuit placed over a number outwardly extending ribs in accordance with an embodiment of the disclosed technology.

In accordance with another aspect of the disclosed technology, some embodiments of the flex circuits 250 include holes or vias 270 that are cut between the electrical traces 252. In one embodiment, the holes 270 are placed between each trace on the flex circuit. In another embodiment, the holes 270 are placed at other spaced intervals (or varying intervals) between the traces of the flex circuit. The holes 270 allow the adhesive that is used to secure the flex circuit 250 to the ribs 202 to squeeze out and form rivet-shaped caps that help secure the flex circuit to the transducer frame. FIG. 8 shows an example of a flex circuit 250 that is secured to a number of ribs 202 on a frame 170. A portion of the adhesive that secures the flex circuit to the ribs on the frame is pressed through the holes 270 to form rivets 276 that help maintain the contact between the ribs and the traces and to help prevent the flex circuit from tearing off the frame 170.

With a high frequency transducer, the transducer elements can be made small enough so that a large array (e.g. 64+ elements) can be included in a small enclosure. As will be appreciated by those skilled in the art, the size of the transducer elements affects the maximum angle at which beamsteering or beamforming can be used with the array. As described above, the connections to the transducer described are small enough so that the entire transducer and connections can be incorporated into intravenous catheters, endoscopes, bronchoscopes, cystoscopes, dental imaging probes or other minimally invasive imaging probes.

Because the width of the flex circuits that connect to the transducer elements is approximately the same width of the transducer (or less), the transducer can be oriented in a forward facing direction in the catheter without having to significantly increase the diameter of the catheter. In one embodiment, excess material on the flex circuits to the sides of the traces can be trimmed off. Therefore, the flex circuits can be made to have a width that is equal to the width of the transducer array or less.

Because the pitch of the transducer elements is small (e.g. preferably less than or equal to 0.75 lambda and more preferably less than about 0.6 lambda), beamsteering or beamforming techniques can be used to obtain ultrasound signals from a variety of directions around the transducer without having to move the transducer more than for example +/−90 degrees. The result is a forward looking phased array ultrasound catheter that allows an operator to view the direction in which the catheter is being advanced as well as being able to view the walls of the tissue surrounding the catheter tip. Furthermore, because the transducer elements are diced by kerf lines, cross talk between individual elements is reduced producing superior signals. In addition, elements may be sub-diced to move lateral mode resonances out of band further reducing cross talk between elements.

From the foregoing, it will be appreciated that specific embodiments of the disclosed technology have been described herein for purposes of illustration, but that various modifications may be made without deviating from the scope of the invention. For example, it is not necessary that the registration features on the frame of the transducer and the flex circuit fit together as a post and a hole. Other shapes such as keys and keyways could be used. Alternatively, posts or other shapes could be secured at known locations on the flex circuit and holes or other shapes could be formed on the frame to align the flex circuits with the ribs on the frame. In addition, the catheter or other minimally invasive medical device can include a side-firing transducer array. If a side-firing array is used, then the larger arrays of 128, 256 or 512 (or more) transducer elements can be used. Accordingly, the invention is not limited except as by the appended claims.

We claim:

1. A probe for inspecting areas of a body comprising:
   a probe body;
   an ultrasound transducer within the probe body, that includes:
   a frame;
   an array of transducer elements having a bottom surface and a top surface that are formed in a sheet of piezoelectric material that is connected to the frame;
   a number of conductive paths that connect one surface of the transducer elements to a circuit trace, wherein each conductive path includes a rib separated from a neighboring rib by a space and each conductive path includes a channel aligned with a respective transducer element and having a recessed depth such that the recessed depth of the channel of each conductive path decreases as the channel extends outwardly from the respective transducer element and becomes the rib of the respective conductive path over a length of the respective conductive path, each rib including a conductive surface that is adapted to engage an exposed portion of a conductive trace, wherein each rib is formed of a powder-filled epoxy that is placed in the frame and each channel is cut from the powder-filled epoxy that is placed in the frame; and
   one or more flex circuits having traces that are connected to the ribs on the transducer.

2. The probe of claim 1, wherein the powder in the powder-filled epoxy is silica.

3. The probe of claim 1, wherein each channel portion is adjacent a respective transducer element of the array of transducer elements.

4. The probe of claim 1, wherein the frame includes one or more registration features that are configured to align with a corresponding feature on at least one of the one or more flex circuits in order to align exposed traces in the flex circuit with the ribs of the frame.

5. The probe of claim 1,
   wherein each rib includes a number of scribe lines formed thereon that increase the surface area on a top of the rib.

6. The probe of claim 1,
   wherein each rib terminates at a same height on the frame of the ultrasound transducer.

7. The probe of claim 1,
wherein at least two ribs of the ultrasound transducer terminate at different heights on the frame of the ultrasound transducer.

8. The probe of claim 1, wherein each trace of at least one of the one or more flex circuits engages a respective rib such that each trace is electrically connected through the conductive surface on top of the respective rib to a transducer element in the array.

9. The probe of claim 8, wherein the at least one of the one or more flex circuits includes a number of holes placed between the traces in an area where the exposed traces engage the ribs, wherein the holes are configured to allow an adhesive to pass through the holes when the flex circuit is adhered to the ribs and form a number of rivet heads.

10. A probe for inspecting areas of a body comprising:
a probe body having an outer diameter of 8 mm. or less;
a forward facing high frequency ultrasound transducer within the probe body, that includes:
    a frame having a width dimension with an epoxy material therein that is formed into a number of outwardly extending ribs having a conductive surface thereon;
    an array of transducer elements having a bottom surface and a top surface that are formed in a sheet of piezoelectric material that is connected to the frame, wherein adjacent transducer elements are separated by kerf lines extending entirely though the piezoelectric material and the transducer elements have a pitch of 0.75 lambda or less and wherein each transducer element is connected by a conductive path, each conductive path including a respective outwardly extending rib on the frame and a channel aligned with a respective transducer element and having a recessed depth such that the recessed depth of the channel of each conductive path decreases as the channel extends outwardly from the respective transducer element and becomes the rib of the respective conductive path over a length of the respective conductive path; and
    one or more flex circuits having traces that are electrically connected to the outwardly extending ribs to create an electrical connection between the traces and the transducer elements on the transducer, wherein the flex circuits have a width that is equal to or less than the width dimension of the frame of the transducer.

11. The probe of claim 10, wherein the frame includes one or more registration features that are configured to align with a corresponding feature on at least one of the one or more flex circuits having electrical conductors therein.

12. The probe of claim 1, wherein each rib extends above a surface of the powder-filled epoxy that is placed in the frame; and each channel extends below the surface of the powder-filled epoxy that is placed in the frame.

13. The probe of claim 1, wherein the probe body comprises a distal end, and wherein the array of transducer elements is oriented toward the distal end of the probe body.

14. The probe of claim 1, wherein adjacent transducer elements are separated by kerf lines extending entirely though the piezoelectric material.

15. The probe of claim 13, wherein the transducer elements have a pitch of 0.75 lambda or less.

16. The probe of claim 10, wherein the probe body comprises a distal end, and wherein the array of transducer elements is oriented toward the distal end of the probe body.

17. The probe of claim 10, wherein each rib is formed of a powder-filled epoxy that is placed in the frame and each channel is cut from the powder-filled epoxy that is placed in the frame.

18. A probe for inspecting areas of a body comprising:
a probe body;
an ultrasound transducer within the probe body, that includes:
    a frame;
    an array of transducer elements having a bottom surface and a top surface that are formed in a sheet of piezoelectric material that is connected to the frame;
    a number of conductive paths that connect one surface of the transducer elements to a circuit trace, wherein each conductive path includes a rib separated from a neighboring rib by a space and each conductive path includes a channel aligned with a respective transducer element and having a recessed depth such that the recessed depth of the channel of each conductive path decreases as the channel extends outwardly from the respective transducer element and becomes the rib of the respective conductive path over a length of the respective conductive path, each rib including a conductive surface that is adapted to engage an exposed portion of a conductive trace, wherein each rib extends above a surface of a powder-filled epoxy that is placed in the frame and each channel extends below the surface of the powder-filled epoxy that is placed in the frame; and
    one or more flex circuits having traces that are connected to the ribs on the transducer.

19. The probe of claim 18, wherein the powder in the powder-filled epoxy is silica.

20. The probe of claim 18, wherein each rib is formed of a powder-filled epoxy that is placed in the frame and each channel is cut from the powder-filled epoxy that is placed in the frame.

* * * * *